United States Patent [19]

Bischof

[11] Patent Number: 5,536,238

[45] Date of Patent: Jul. 16, 1996

[54] SYSTEMS AND METHODS FOR SIMULTANEOUSLY REMOVING FREE AND ENTRAINED CONTAMINANTS IN FLUIDS LIKE BLOOD USING PHOTOACTIVE THERAPY AND CELLULAR SEPARATION TECHNIQUES

[75] Inventor: Daniel F. Bischof, McHenry, Ill.

[73] Assignee: Baxter International Inc., Deerfield, Ill.

[21] Appl. No.: 289,175

[22] Filed: Aug. 11, 1994

Related U.S. Application Data

[63] Continuation of Ser. No. 215,968, Mar. 17, 1994, abandoned, which is a continuation of Ser. No. 55,915, Apr. 29, 1993, abandoned, which is a continuation of Ser. No. 630,864, Dec. 20, 1990, abandoned.

[51] Int. Cl.$^6$ .................................................. A61M 37/00
[52] U.S. Cl. ................................. 604/6; 604/4; 422/44; 210/748; 210/767
[58] Field of Search ...................... 604/4–6, 20, 49; 128/898; 424/529–534; 210/748, 767; 422/186.3, 22, 44

[56] References Cited

U.S. PATENT DOCUMENTS

| | | |
|---|---|---|
| 2,308,516 | 1/1943 | Knott . |
| 3,462,361 | 8/1969 | Greenwalt et al. ...................... 422/44 |
| 4,181,128 | 1/1980 | Swartz . |
| 4,321,919 | 3/1982 | Edelson .................................. 604/20 |
| 4,398,906 | 8/1983 | Edelson .................................. 604/6 |
| 4,402,318 | 9/1983 | Swartz . |
| 4,428,744 | 1/1984 | Edelson .................................. 604/20 |
| 4,456,512 | 6/1984 | Bieler et al. . |
| 4,573,962 | 3/1986 | Troutner . |
| 4,596,657 | 6/1986 | Wisdom .................................. 210/206 |
| 4,612,007 | 9/1986 | Edelson .................................. 604/20 |
| 4,613,322 | 10/1986 | Edelson . |
| 4,683,989 | 8/1987 | Edelson .................................. 604/6 |
| 4,684,521 | 8/1987 | Edelson . |
| 4,705,498 | 11/1987 | Goss . |
| 4,708,715 | 11/1987 | Troutner et al. . |
| 4,727,027 | 2/1988 | Wiesehahn et al. . |
| 4,737,140 | 4/1988 | Lee et al. . |
| 4,769,131 | 9/1988 | Noll et al. . |
| 4,775,625 | 10/1988 | Sieber . |
| 4,787,883 | 11/1988 | Kroyer .................................. 604/4 |
| 4,822,335 | 2/1989 | Kawai et al. . |
| 4,838,852 | 6/1989 | Edelson et al. . |
| 4,878,891 | 11/1989 | Judy et al. . |
| 4,889,129 | 1/1990 | Dougherty et al. . |
| 4,915,638 | 4/1990 | Sieber . |
| 4,921,473 | 5/1990 | Lee et al. ............................... 422/44 |
| 4,950,225 | 8/1990 | Davidner et al. ...................... 604/4 |
| 4,983,307 | 1/1991 | Nesathurai . |
| 4,997,577 | 3/1991 | Stewart ................................. 604/410 |
| 5,030,200 | 7/1991 | Judy et al. . |
| 5,032,241 | 7/1991 | Robertson et al. . |
| 5,069,885 | 12/1991 | Ritchie . |
| 5,078,673 | 1/1992 | Abrams .................................. 604/4 |

FOREIGN PATENT DOCUMENTS 0138489  7/1985  European Pat. Off. .

OTHER PUBLICATIONS

Matthews et al., "Photodynamic Theray of Viral Contaminants with Potential for Blood Banking Applications", *Transfusion*, v. 28, 1 1988 p. 81–83.

Primary Examiner—John D. Yasko
Assistant Examiner—Mark Bockelman
Attorney, Agent, or Firm—Daniel D. Ryan; Bradford R. L. Price; Joseph B. Barrett

[57] ABSTRACT

Systems and methods remove a contaminant from a fluid like blood, regardless of whether the contaminant is carried free within the fluid or entrained within cellular matter carried within the fluid. The systems and methods rely upon photodynamic processes to remove free contaminants from the fluid. The systems and methods rely upon separation processes to remove the cellular matter and, with it, the contaminants it entrains from the fluid.

2 Claims, 3 Drawing Sheets

SYSTEMS AND METHODS FOR SIMULTANEOUSLY REMOVING FREE AND ENTRAINED CONTAMINANTS IN FLUIDS LIKE BLOOD USING PHOTOACTIVE THERAPY AND CELLULAR SEPARATION TECHNIQUES

This is a continuation of application Ser. No. 08/215,968 filed on Mar. 17, 1994, now abandoned, which is a Continuation of Ser. No. 08/055,915 filed on Apr. 29, 1993, now abandoned, which is a Continuation of Ser. No. 07/630,864 filed on Dec. 20, 1990 (Abandoned).

FIELD OF THE INVENTION

The invention generally relates to the eradication of contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immunodeficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components. See Matthews et al, "Photodynamic Therapy of Viral Contaminants With Potential for Blood Bank Applications," *Transfusion*, 28(1), pp. 81–83 (1988). Various extracorporeal systems have been proposed that use photodynamic therapy to treat blood prior to storage and transfusion. See, for example, Edelson U.S. Pat. Nos. 4,613,322 and 4,684,521; Troutner et al U.S. Pat. No. 4,708,715; Wiesehahn et al U.S. Pat. No. 4,727,027; Sieber U.S. Pat. Nos. 4,775,625 and 4,915,683; and Judy et al U.S. Pat. No. 4,878,891.

To date, there has been a general lack of success in economically adapting the benefits of photodynamic therapy to the demands of the blood banking industry. One reason for this is that not all biological contaminants are carried free within the blood where they can be readily coupled to photoactive agents. Some biological contaminants are entrained on or within white blood cells out of the reach of photoactive agents.

The extracorporeal systems proposed to date can eradicate only contaminants that are carried free within the blood. Prior systems have not provided a device that can remove both free and entrained biological contaminants from a fluid in a single pass through a single treatment zone.

For this and other reasons, the promise of photodynamic therapy in treating the nation's banked blood supply has gone largely unfulfilled.

SUMMARY OF THE INVENTION

The invention provides improved systems and methods for removing all contaminants from a fluid like blood, regardless of whether the contaminants are carried free within the fluid or are themselves entrained within cellular matter carried within the fluid. The invention relies upon photodynamic therapy to remove free contaminants from the fluid. The invention relies upon cellular separation techniques to remove the cellular matter in which contaminants are entrained.

In one aspect of the invention, the invention provides a treatment chamber into which the fluid is conveyed. A first element in the interior chamber removes entrained contaminants by separating from the fluid the cellular component in which contaminants are entrained.

A second element in the interior chamber emits radiation at a selected wavelength to activate a photoactive material previously bound to the free contaminants. The activated photoactive material eradicates the free contaminants.

The invention thereby provides a single treatment chamber where the eradication or removal of both intercellular and intracellular contaminants present within a fluid can be accomplished.

In one embodiment, the first element uses filtration as the separation technique. In a preferred embodiment, the first element employs filtration through a bed of filter material.

In one embodiment, the second element uses photodiodes as the radiation source. In another embodiment, the second embodiment uses optical fibers as the radiation source.

In a preferred arrangement, the second element includes spaced apart first and second arrays of radiation sources located along the flow path of the fluid within the chamber. In this arrangement, the filtration material that forms the first element is sandwiched between the first and second radiation arrays in the fluid flow path. The fluid in the path is thereby simultaneously filtered and irradiated.

In another preferred embodiment, the first element also comprises filtration material located in the path of fluid flow. In this arrangement, the second element includes a least one optical fiber having a light emitting surface that extends within the filtration material. Again, the fluid is both irradiated and filtered in a single pass through a single treatment zone.

Another aspect of the invention provides a method for treating a fluid carrying contaminants that are both free and entrained within cellular matter. In this aspect of the invention, a photoactive material is added to the fluid. The photoactive material binds itself to the free contaminants. The fluid is conveyed along a fluid path. While being conveyed along the path the cellular component that entrains contaminants is separated from the fluid. The entrained contaminants are also thereby removed. At the same time, radiation is emitted into the fluid path at a selected wavelength to activate the bound photoactive material and thereby eradicate the free contaminant.

The invention is well suited for blood processing applications. In these applications, the invention serves to remove contaminants either carried free in the plasma (by photodynamic therapy) or entrained within white blood cells (by separation techniques like filtration).

Other features and advantages of the invention will be pointed out in, or will be apparent from, the drawings, specification and claims that follow.

Figure 1:
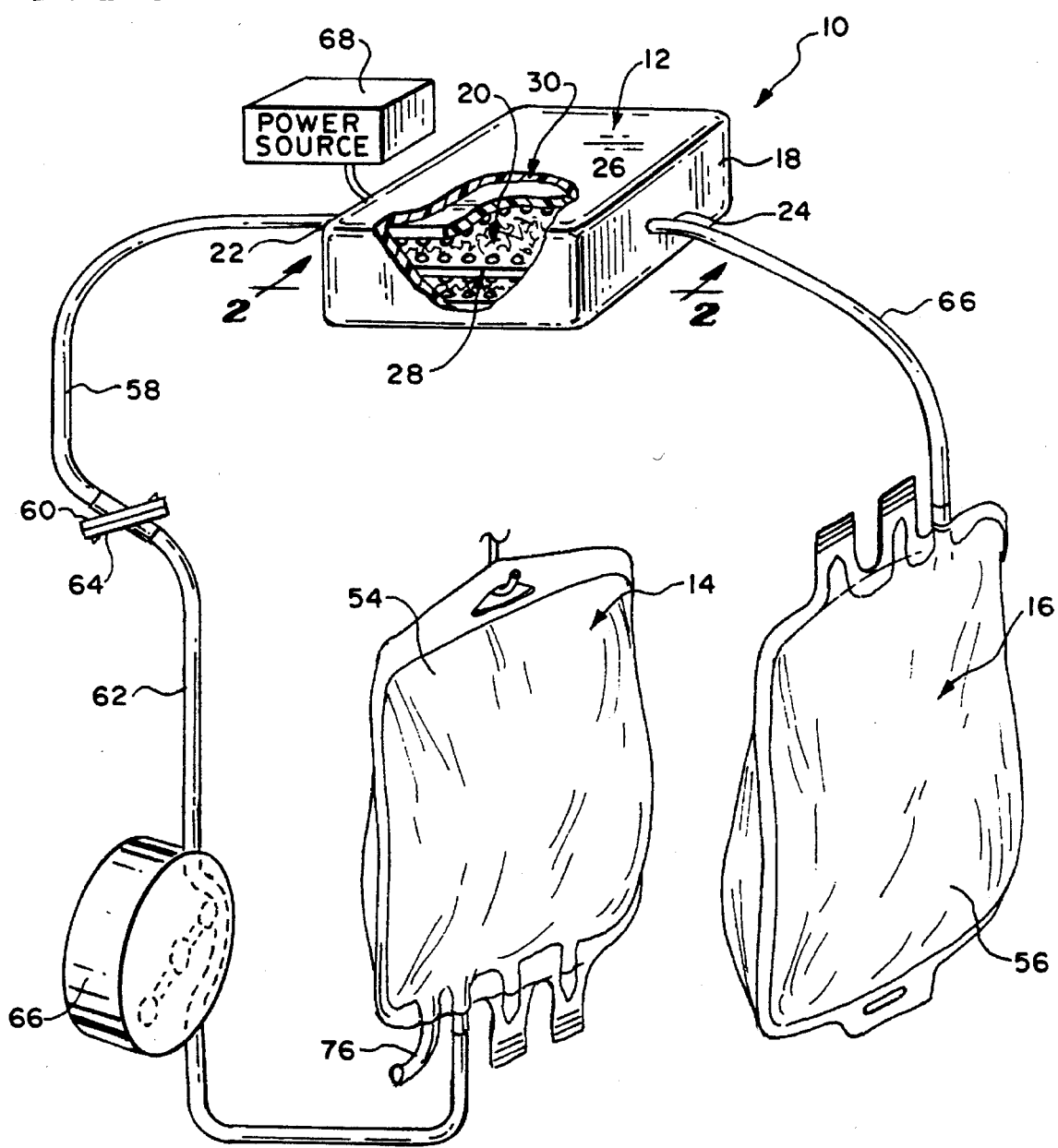
FIG. 1 is a perspective view, with portions broken away, of a system for treating a fluid carrying a contaminant that embodies the features of the invention.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a system 10 for treating a fluid carrying contaminants that embodies the features of the invention. The contaminants are either carried free within the fluid or they are entrained on or within cellular matter that the fluid contains. According to the invention, the system 10 simultaneously removes both types of contaminants from the fluid within a single treatment zone.

The system 10 includes a treatment device 12 that receives the fluid from a source container 14 and conveys the fluid after treatment to a collection container 16.

The system 10 can treat various types of fluid. In the illustrated embodiment, the fluid comprises a suspension that includes at least one therapeutic component of whole human blood that is intended to be stored for transfusion. More specifically, the fluid consists of principally of red blood cells suspended in plasma. However, suspension also contains a quantity of white blood cells that are not be separated from the red blood cells using typical separation techniques. The fluid can also include an anticoagulant and, optionally, a storage medium for the blood component. Alternatively, the fluid can consist of platelets and a quantity of white blood cells suspended in plasma.

In the illustrated embodiment, the contaminant comprises a pathogenic virus typically carried in the blood. For example, the contaminant can consist of the hepatitis-B virus; the human immunodeficiency virus; the Herpes virus; or the influenza virus.

The white blood cells in the suspension are capable of ingesting or entraining such biological contaminants to remove them from the plasma. The contaminants that are not entrained by the white blood cells remain free in the plasma.

The treatment device 12 includes housing 18 that encloses an interior chamber 20. The chamber 20 has an inlet 22 for receiving the blood suspension from the source container 14 and an outlet 24 for discharging the blood suspension into the collection container 16.

The device 12 includes a first element 26 in the interior chamber 20 for removing the biological contaminants that are entrained within the white blood cell component. In the illustrated embodiment, the first element 26 serves to separate the cellular white blood cell component, and with it, the contaminant by filtration. However, it should be appreciated that the first element 26 can remove the cellular component by various centrifugal and non-centrifugal techniques, and not merely "filtration" in the technical sense. Separation of cellular matter can occur by absorption, columns, chemical, electrical, and electromagnetic means, and not just by filtration.

In the illustrated embodiment, the first element 26 includes conventional filtration medium for removing white blood cells from the blood. The filtration medium 26 can include cotton wool, cellulose acetate, or another synthetic fiber like polyester.

The filtration medium 26 can remove the white blood cells by conventional depth filtration techniques, or by conventional screen filtration techniques, or by surface specific filtration, by a combination of these techniques. In the illustrated embodiment, the filtration medium 26 comprises a bed of polyester fibers that entraps white blood cells using principally depth filtration.

The device 12 further includes a second element 28 in the interior chamber 20 for removing the biological contaminants that are carried free within the plasma, that is, outside the white blood cells. In the illustrated embodiment, the second element 28 employs photodynamic therapy to remove the free biological contaminants.

More particularly, the suspension in the source container 14 includes a photoactive material that has an affinity for the biological contaminant carried free within the plasma. The photoactive material is added to the blood suspension in the source container 14 in a preliminary step that will be described in greater detail later.

Due to its affinity for the contaminant, the photoactive material becomes bound to the contaminant carried free within the source container 14. The photoactive material is of a type that becomes active by exposure to radiation within a prescribed wavelength range. When activated by radiation, the material eradicates the contaminant.

Various types of photoactive materials can be used. In the illustrated embodiment, the photoactive compound comprises a family of light-activated drugs derived from benzoporphyrin. These derivatives are commonly referred as BPD's. BPD's are commercially available from Quadra Logic Technologies, Inc., Vancouver B.C., Canada.

BPD's, like other types of hematoporphyrin materials, have an affinity for the cell walls of many viral organisms that are carried in blood. They therefore bind or attach themselves to the biological cell wall of these organisms. When exposed to radiation, BPD's undergo an energy transfer process with oxygen, forming a singlet oxygen. When the singlet oxygen oxidizes, it kills the biological cells to which it has attached. BPD's are described in greater detail in Judy et al U.S. Pat. No. 4,878,891.

In the illustrated embodiment, the second element 28 emits radiation at a selected wavelength to activate the photoactive material bound to the biological contaminant. The second element 28 can be variously constructed. The drawings show three possible alternative embodiments.

Figure 2:
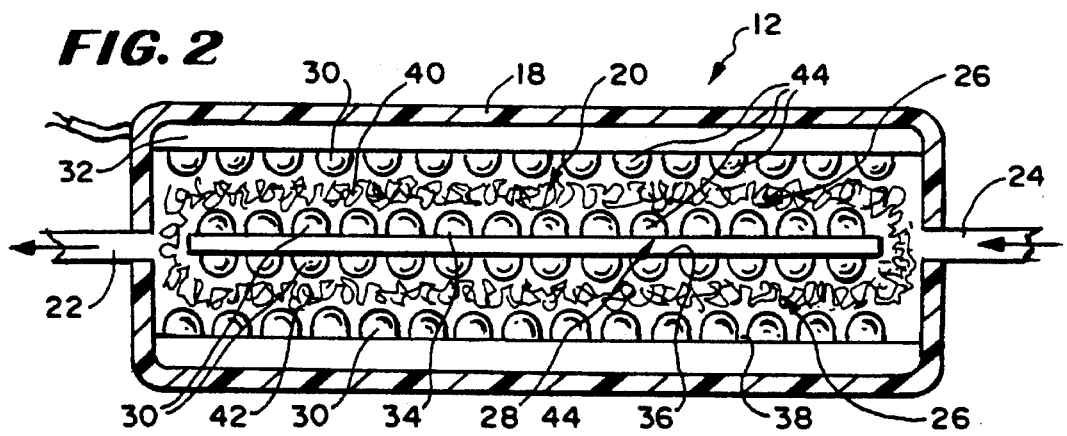
FIG. 2 is a section view of the treatment device associated with the system shown in FIG. 1, taken generally along line 2—2 in FIG. 1.

In the embodiment shown in FIGS. 1 and 2, the second element 28 includes one or more arrays 30 of radiation sources located along the flow path of the fluid between the inlet and outlet 22 and 24 of the chamber 20. The filtration medium 26 extends within these arrays 30. An external power element 68 is coupled to the arrays 30 for controlling their operation.

More particularly, the second element 28 includes four spaced apart banks 32, 34, 36, and 38 (see FIG. 2) of radiation sources located along the flow path of the fluid between the inlet and outlet 22 and 24 of the chamber 20. The banks 32 and 34 face each other, forming a first fluid branch path 40 between themselves. The other two banks 36 and 38 also face each other and between them form a second fluid branch path 42. In this arrangement, the filtration medium 26 occupies each branch path 40 and 42.

Each bank 32, 34, 36, and 38 comprises an arrangement of several discrete radiation sources 44. Each radiation source 44 is "discrete," meaning that each source 44 is a self-contained emitter of radiation that establishes its own zone of radiation. Being discrete, each source 44 also is capable of operation to emit a radiation independent of the emission of radiation by the other sources 44, if desired.

In the illustrated and preferred embodiment, each radiation source 44 takes the form of a photodiode. Various types of photodiodes can be selected, depending upon the fluid treated and the characteristics of the photoactive material used. In the illustrated embodiment, where the treated fluid contains red blood cells, all the photodiodes use transparent substrate aluminum gallium arsenide material (TS AlGaAs). Photodiodes of this type are commercially available from Hewlett-Packard Co. (Product designation HLMP-8150 15 Candella).

These photodiodes emit a band of radiation at a relatively narrow viewing angle of about 4 degrees. The prescribed band of radiation has a relatively precise wavelength displaying a red color having a peak wavelength of about 690 nm. Red blood cells are essentially transparent to radiation at this wavelength. The BPD's, however, are not. The BPD's absorb radiation in this wavelength to become activated.

If the blood suspension includes platelets, the photodiode would be selected to have a wavelength displaying a blue color having peak wavelength of about 425 nm. Platelets are essentially transparent to radiation at this wavelength.

In the illustrated embodiment, each discrete photodiode radiation source operates has a minimum intensity of about 8.0 cd (at 20 mA), a maximum intensity of about 36.0 cd (at 20 mA), and a typical intensity of about 15.0 cd (at 20 mA). Each photodiode operates at a low maximum forward voltage of about 2.4 V.

Figure 3:
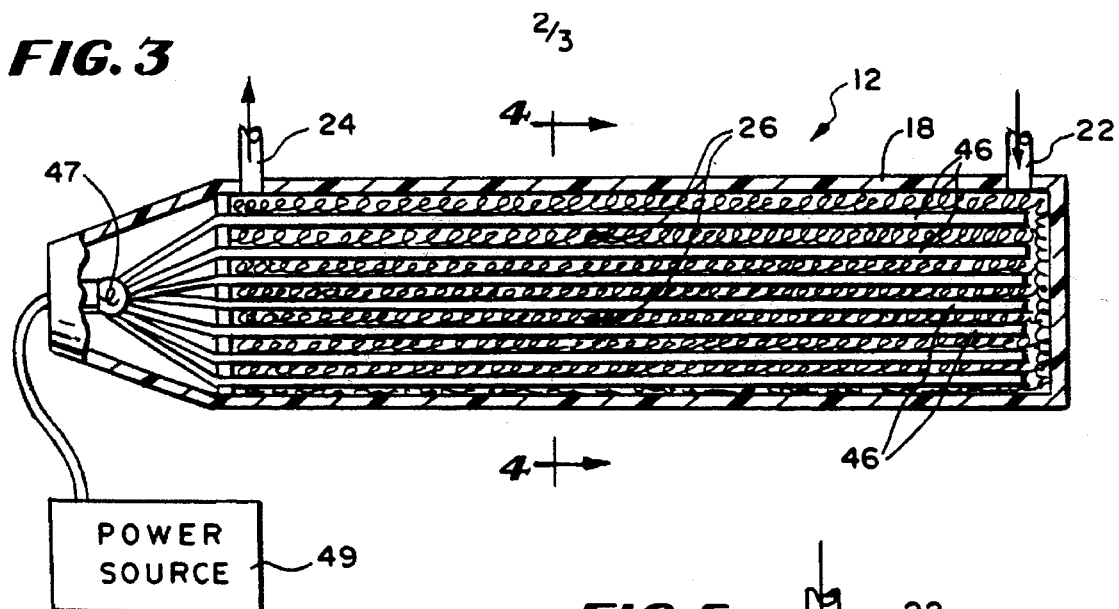
FIG. 3 is a section view of another embodiment of a treatment device that can be used in association with the system showing in FIG. 1.
Figure 4:
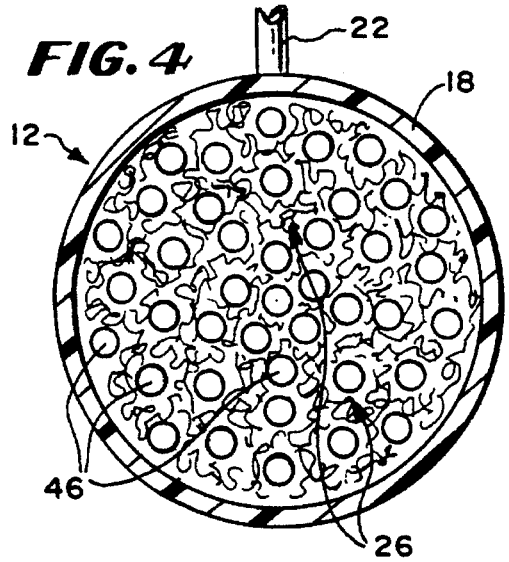
FIG. 4 is a view of the treatment device taken generally along line 4—4 in FIG. 3.

FIGS. 3 and 4 show an alternative embodiment. In this embodiment, at least one optical fiber 46 having a light emitting region 48 that extends within the filtration medium 26. As shown, an array of several optical fibers 46 extends within the filtration medium 26 (see FIG. 4), deriving their radiation from a single source 47. An external element 49 powers and controls the operation of the source 47.

In this arrangement, the cladding of each optical fiber 46 is removed in the region 48 where it extends into the filtration medium 26. The fibers 46 therefore emit radiation along this region 48.

Figure 5:
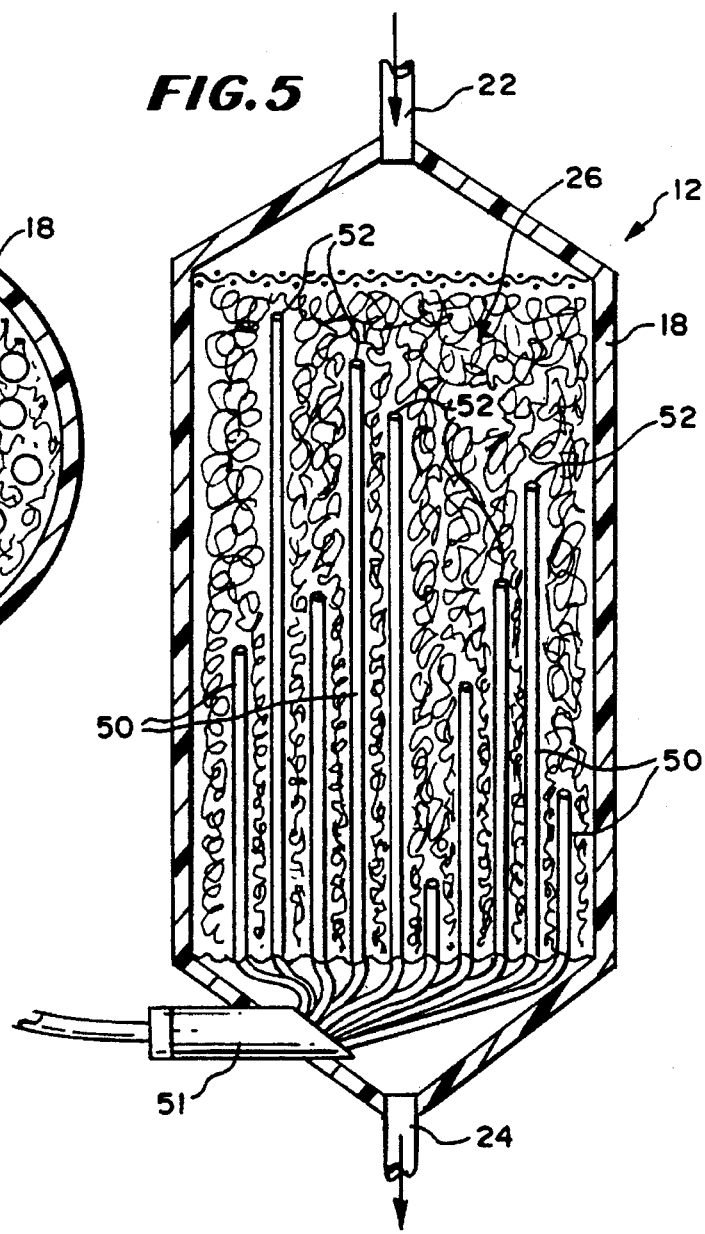
FIG. 5 is a section view of another embodiment of a treatment device that can be used in association with the system showing in FIG. 1.

FIG. 5 shows another alternative embodiment. In this embodiment, as in the embodiment shown in FIGS. 3 and 4, an array of several optical fibers 50 extends within the filtration medium. As in the FIGS. 3 and 4 arrangement, the fibers 50 derive their radiation from a single source 51. An external element (not shown) powers and controls the operation of the source 51 as in the FIGS. 3 and 4 embodiment.

Unlike the embodiment shown in FIGS. 3 and 4, the cladding of each optical fiber 50 remains in place, except at the tip end 52. The fibers 50 therefore emit radiation only from their tip ends 52. In this arrangement, the fibers 50 extend at different lengths within the filtration medium 26 to assure a uniform dispersal of radiation along the fluid path.

In the illustrated embodiment, the source container 14 and the collection container 16 each takes the form of a bag (respectively 54 and 56) made of a flexible inert plastic material, like plasticized medical grade polyvinyl chloride.

Figure 6:
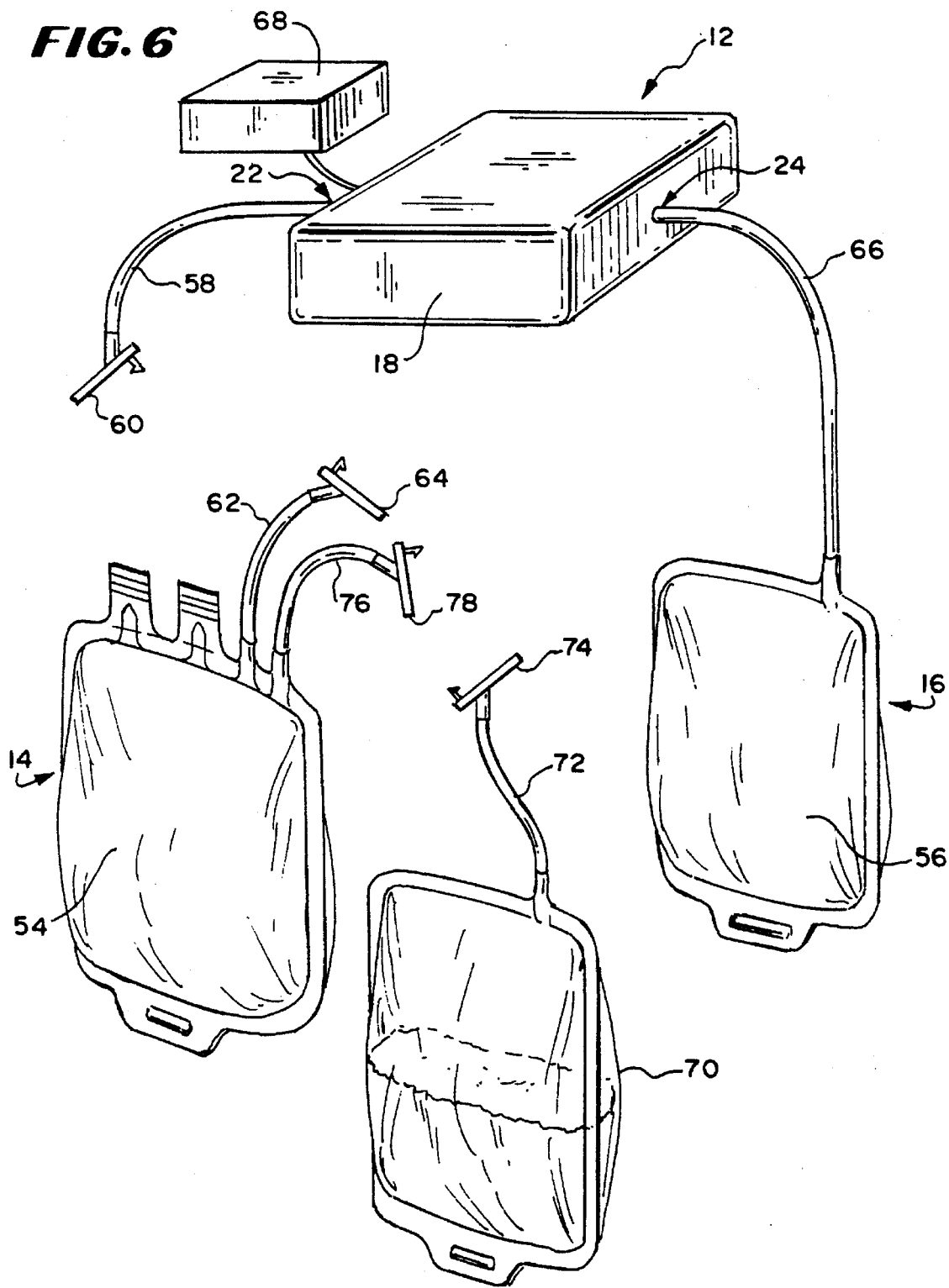
FIG. 6 is a perspective view of the component parts of the system shown in FIG. 1, with the component parts disassembled prior to use.

In the illustrated embodiment (see FIG. 6), the inlet 22 to the treatment device 12 includes a length of flexible inert plastic tubing 58. The tubing 58 terminates in a first connection device 60.

A length of flexible inert plastic tubing 62 also joins the source container 14. This tubing 62 includes a second connection device 64 that mates with the first connection device 60 to join the source container 14 to the inlet 22 of treatment device 12 (as FIG. 1 shows).

While various known connection devices may be used, in the illustrated embodiment, the devices 60 and 64 are preferable sterile connection devices like those shown in Granzow et al U.S. Pat. Nos. 4,157,723 and 4,265,280, which are incorporated herein by reference.

In use, a peristaltic pump 66 (see FIG. 1) conveys fluid through into the treatment device 12 at a predetermined flow rate.

The outlet 24 of the treatment device 12 also includes a length of flexible inert plastic tubing 66. The end of the tubing 66 joins the collection container 16. In an alternative arrangement (not shown), the tubing 66 could be normally separated into two lengths, like tubings 58 and 62, each having a sterile connection device to join the collection container 16 to the outlet 24 of the treatment device 12 prior to use.

In the illustrated embodiment (see FIG. 6), an auxiliary container 70 holds a solution containing the photoactive material. The auxiliary container 70 also includes a length of tubing 72 that carries with a third (preferably sterile) connection device 74. In this arrangement, the source container 14 also includes another length of tubing 76 that carries a fourth (preferably sterile) connection device 78. By joining the third and fourth sterile connection devices 74 and 78, the photoactive material can be conveyed from the auxiliary container 70 into the source container 14 for mixing with the fluid to be treated. The joined tubings 72 and 76 form a closed, internally sterile path for introducing the photoactive materially into the source container 14. Once the photoactive material has been transferred, the tubing 76 can be heat sealed closed downstream of the joined connection devices 74 and 78 (as FIG. 1 shows), and the auxiliary container 70 removed.

By using the sterile connection devices 60, 64, 74, and 78, the formed flow path comprises a closed, internally sterile path for conveying fluid from the source container 14, through the treatment chamber 20, and into the collection container 16.

After treatment, the tubing 66 can be heat sealed closed and the collection container 16 removed for storage.

In use, the device 12 can be used to treat a fluid carrying biological contaminants, including those biological contaminants that are entrained within a cellular component carried within the fluid.

In using the device 12, a photoactive material is added to the fluid. The photoactive material binds to the biological contaminants that not entrained by the cellular component. Next, the fluid is conveyed into the device 12 along a predetermined path. As the fluid flows along the path within the device 12, the cellular component capable of entraining biological contaminants is removed by filtration from the fluid. At the same time, radiation is emitted at a selected wavelength into the fluid path within the device 12 to activate the photoactive material and thereby eradicate the contaminant that is not entrained within the cellular component.

Features and advantages of the invention are set forth in the following claims.

I claim:

1. A method of treating a suspension of blood cells to remove biological contaminants comprising the steps of collecting a suspension of blood cells including plasma, white blood cells, and at least one additional therapeutic blood component, the suspension further including biological contaminants, a portion of which are carried free in the plasma and are thereby subject to eradication by photoactive therapy and the remainder of which are entrained by the white blood cells and are thereby not subject to eradication by photoactive therapy, and removing the biological contaminants by adding to the suspension a photoactive material that binds to the portion of biological contaminants that are carried free in the plasma, and emitting radiation at a selected wavelength into a filtering chamber to activate the photoactive material bound to the freely carried biological contaminants to eradicate the portion of the biological contaminants that are not entrained by the white blood cells while filtering the suspension to remove the white blood cells from the suspension, thereby removing with them the entrained biological contaminants.

2. A method according to claim 1 and further including the step of storing the suspension after emitting radiation to eradicate the free biological contaminants and after filtration to remove the entrained biological contaminants.

* * * * *